United States Patent [19]

De Knaep et al.

[11] Patent Number: 5,463,049
[45] Date of Patent: Oct. 31, 1995

[54] PROCESS FOR PREPARING ENANTIOMERICALLY PURE IMIDAZO[4,5,1-JK][1,4]-BENZODIAZEPIN-2(1H)-THIONES

[75] Inventors: Alfons G. M. De Knaep, Turnhout; Luc J. R. Moens, Lille; Eduard J. C. Vreysen, Mol, all of Belgium

[73] Assignee: Janssen Pharmaceutica N.V., Beerse, Belgium

[21] Appl. No.: 196,168

[22] PCT Filed: Sep. 18, 1992

[86] PCT No.: PCT/EP92/02171

§ 371 Date: Feb. 15, 1994

§ 102(e) Date: Feb. 15, 1994

[87] PCT Pub. No.: WO93/06106

PCT Pub. Date: Apr. 1, 1993

[30] Foreign Application Priority Data

Sep. 24, 1991 [EP] European Pat. Off. .............. 9120247

[51] Int. Cl.[6] ............................................. C07D 487/04
[52] U.S. Cl. .................................................... 540/556
[58] Field of Search ....................................... 540/556

[56] References Cited

FOREIGN PATENT DOCUMENTS

| 0384522 | 9/1990 | European Pat. Off. . |
| 4036552C1 | 2/1992 | Germany . |
| WO85/04403 | 10/1985 | WIPO . |
| WO92/13860 | 8/1992 | WIPO . |

*Primary Examiner*—John M. Ford
*Attorney, Agent, or Firm*—Charles J. Metz

[57] ABSTRACT

Process for preparing enantiomerically pure imidazo[4,5,1-jk][1,4]benzodiazepin-2(1H)-thiones of formula

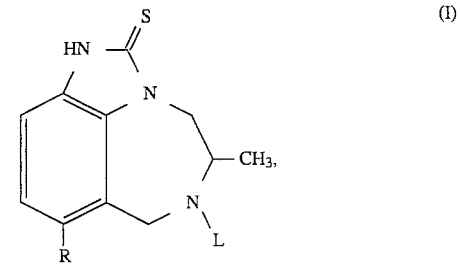

starting from 2,6-dihalo-3-nitrobenzyl derivatives (II) and suitably N-protected 1,2-diaminopropanes (III)

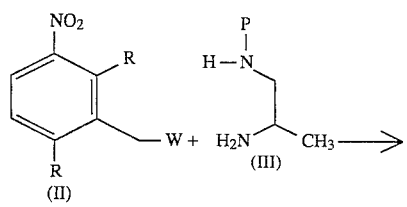

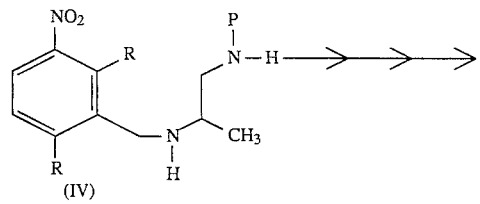

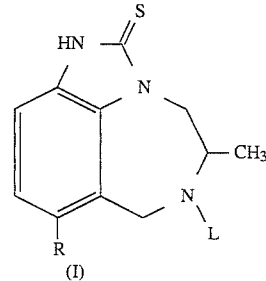

Novel enantiomerically pure intermediates of formula (III) and (IV) prepared in the course of the present process.

10 Claims, No Drawings

PROCESS FOR PREPARING ENANTIOMERICALLY PURE IMIDAZO[4,5,1-JK][1,4]-BENZODIAZEPIN-2(1H)-THIONES

CROSS-REFERENCE TO RELATED APPLICATIONS

This application is based upon PCT application No. PCT/EP 92/02171, filed Sep. 18, 1992, which claims priority from EPO application Ser. No. 91.202.474.2, filed Sep. 24, 1991.

BACKGROUND OF THE INVENTION

In EP-A-0,348,522; Nature 1990, 343, 470; J. Med. Chem. 1991, 34, 746; and The Lancet 1991, 338, 140 there are described 4,5,6,7-tetrahydroimidazo[4,5,1-jk]-[1,4]benzodiazepin-2(1H)-thiones (TIBO) derivatives with potent activity against human immunodeficiency virus 1 (HIV-1) in vitro and showing encouraging results in vivo. A significant limitation to further assessment and eventual large-scale production of these novel drugs has hitherto been their long, difficult and insufficient synthesis. The fundamental problem in all approaches to the title compounds reported up till now relates to the use of benzoic acid derivatives and/or amino acid derivatives as starting materials. All said approaches necessarily involve one or two amide-to-amine reduction steps with violently reacting reagents such as lithium aluminum hydride or borane derivatives. Whereas such approaches may be suitable in the laboratory, (e.g.J. Org. Chem. 1991, 56, 4600), they are hardly amenable to large-scale production. In case enantiomeric amino acid derivatives are used as starting materials, the problems are further compounded by the possibility of racemisation at the chiral carbon atom.

The present invention is concerned with an improved process for preparing particular TIBO derivatives that avoids all problematic amide-to-amine reductions and rules out any possibility of racemisation at the chiral carbon atom. The process according to the present invention also represents a short and efficient industrial approach to particular TIBO compounds reported hitherto.

DESCRIPTION OF THE INVENTION

The present invention is concerned with a process of preparing enantiomerically pure 8-halo-4,5,6,7-tetrahydro-5-methylimidazo[4,5,1 -jk]-[ 1,4]benzodiazepin-2(1H)-thione derivatives having the formula

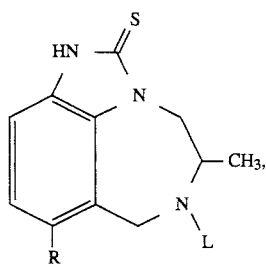
(I)

and the pharmaceutically acceptable acid addition salt forms thereof, wherein

R represents halo; and

L represents $C_{3-7}$alkenyl.

Said process is especially interesting for the preparation of (S)-8-halo-4,5,6,7-tetrahydro-5-methylimidazo[4,5,1- jk] [1,4]benzodiazepin-2(1H)-thione derivatives having the formula

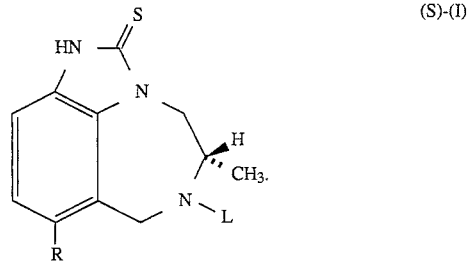
(S)-(I)

and the pharmaceutically acceptable acid addition salt forms thereof, wherein

R in particular represents chloro or bromo; and

L in particular represents 3-methyl-2-butenyl or 3-ethyl-2-pentenyl.

The process according to the present invention is exceedingly interesting for the preparation of (S)-8-chloro-4,5,6,7-tetrahydro-5-methyl-6-(3-methyl-2-butenyl)-imidazo[ 4,5, 1-jk][1,4]benzodiazepine-2(1H)-thione having the formula

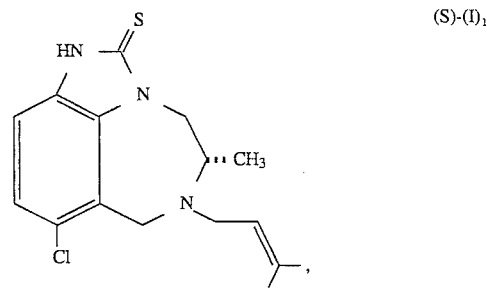
(S)-(I)₁

In the foregoing definitions and hereinafter the term 'enantiomerically pure' concerns compounds having an enantiomeric excess of at least 94% (i.e. minimum 97% of one enantiomer and maximum 3% of the other enantiomer) up to an enantiomeric excess of 100% (i.e. 100% of one enantiomer and none of the other), in particular compounds having an enantiomeric excess of 96% up to 100%, more in particular having an enantiomeric excess of 98% up to 100%; the term 'halo' defines fluoro, chloro, bromo, iodo, in particular chloro or bromo and especially chloro; the term '$C_{3-7}$alkenyl' defines straight and branched hydrocarbon radicals containing one double bond and having from 3 to 7 carbon atoms such as, for example, 2-propenyl, 2-butenyl, 3-butenyl, 2-methyl-2-propenyl, 3-methyl-2-butenyl, 3-ethyl-2-pentenyl and the like, in particular 3-methyl-2-butenyl and 3-ethyl-2-pentenyl. The compounds of formula (I) have basic properties and, consequently, they may be convened to their therapeutically active non-toxic acid addition salt forms by treatment with appropriate acids, such as, for example, inorganic acids, e.g. hydrochloric, hydrobromic and the like acids, sulfuric acid, nitric acid, phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxy-benzoic and the like acids. Conversely the salt form can be converted by treatment with alkali into the free base form. The term pharmaceutically acceptable acid addition salts also comprises the solvates which the compounds of formula (I) may form. Examples of such solvates are e.g. the hydrates, alcoholates and the like.

In particular, the present invention concerns a process of preparing the compounds of formula (I) as defined hereinabove, characterized by (o) selectively protecting enantiomerically pure 1,2-diaminopropane by reaction with a protecting agent of formula P—W, wherein P represents a protective group such as, for example, a sulfonyl group, e.g. methanesulfonyl, trifluoromethanesulfonyl, benzenesulfonyl, 2- or 4-nitrobenzenesulfonyl, 4-methylbenzenesulfonyl, 2,6-dimethylbenzenesulfonyl and the like, or an acyl group, e.g. formyl, methylcarbonyl, tert. butylcarbonyl and the like, and W represents a reactive leaving group such as, for example, halo, e.g. chloro, bromo or iodo, or a sulfonyloxy group, e.g. methanesulfonyloxy, trifluoromethanesulfonyloxy, benzenesulfonyloxy, 4-methylbenzenesulfonyloxy, 2-naphthalenesulfonyloxy and the like leaving groups, optionally in a reaction-inert solvent, to yield an intermediate of formula (III),

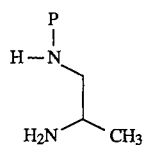
(III)

(i) reacting a 2,6-dihalo-3-nitrobenzyl derivative of formula (II) wherein R represents halo as defined hereinbefore and W represents a reactive leaving group such as, for example, halo, e.g. chloro, bromo or iodo, or a sulfonyloxy group, e.g. methanesulfonyloxy, trifluoromethanesulfonyloxy, benzenesulfonyloxy, 4-methylbenzenesulfonyloxy, 2-naphthalenesulfonyloxy and the like leaving groups, with an enantiomerically pure $N^1$-protected 1,2-diaminopropane derivative of formula (III) in a reaction inert solvent, such as, for example, a halogenated hydrocarbon, e.g. dichloromethane, trichloromethane, an ether, e.g. tetrahydrofuran, 1,4-dioxane, an alcohol, e.g. propanol, 1-butanol, 4-methyl-2-pentanol, a dipolar aprotic solvent, e.g. N,N-dimethylformamide, N,N-dimethylacetamide, dimethyl sulfoxide, and the like, or a mixture of such solvents in the presence of a base such as, for example, an alkali metal carbonate or hydrogen carbonate, e.g. sodium carbonate or sodium hydrogen carbonate, or an organic base such as, for example, N,N-diethylethanamine, N-(1-methylethyl)-2-propanamine and the like,

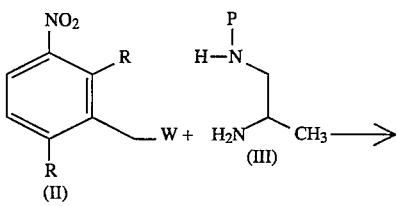

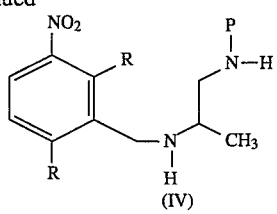
(IV)

(ii) deprotecting the thus obtained intermediate of formula (IV) in an acidic medium such as, for example, hydrobromic acid or preferably, concentrated sulfuric acid, by hydrolysis, thus yielding an intermediate of formula (V), which optionally may be isolated as an acid addition salt,

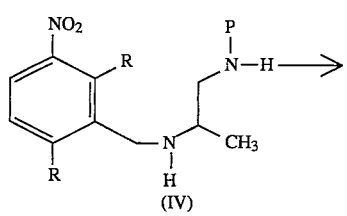

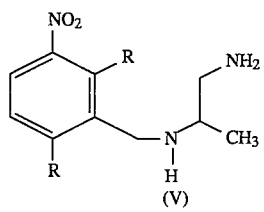
(V)

(iii) cyclizing the amine of formula (V) or an acid addition salt form thereof to a benzodiazepine of formula (VI) by treatment with a base such as, for example, an alkali or earth alkaline metal carbonate, hydrogen carbonate or hydroxide, e.g. sodium carbonate or preferably sodium hydroxide, or an organic amine, e.g. N,N-diethylethanamine and the like, in a reaction-inert solvent such as, for example, an alkanol, e.g. methanol, ethanol, 2-propanol, 1-butanol and the like, a halogenated hydrocarbon, e.g. dichloromethane, trichloromethane and the like, an aromatic hydrocarbon, e.g. benzene, methylbenzene, dimethylbenzene and the like, or a mixture of said solvents, preferably at an elevated temperature, in particular the reflux temperature of the reaction mixture,

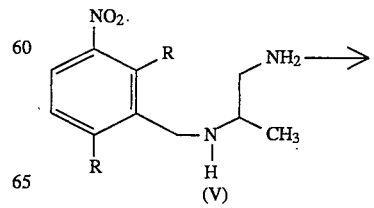

-continued

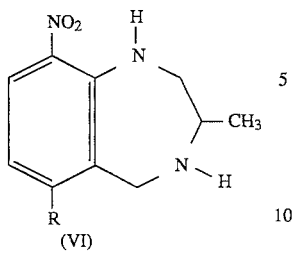
(VI)

(iv) N-alkylating the intermediate of formula (VI) with an alkylating reagent of formula L—W (VII) wherein L is $C_{3-7}$alkenyl as defined under formula (I) and W represents a reactive leaving group such as halo or a sulfonyloxy group, in a manner known per se, i.e. in a reaction-inert solvent in the presence of a base and optionally in the presence of an alkali metal iodide, at an elevated temperature, ranging from about 40° C. to the reflux temperature of the reaction mixture, preferably at about 50° C.,

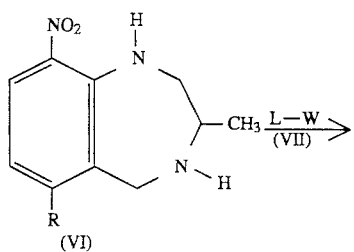
(VI)

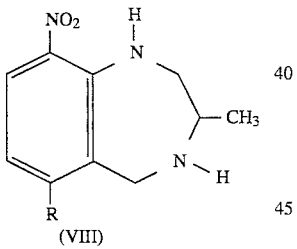
(VIII)

(v) selectively reducing the nitrogroup in (VIII) with a reducing agent to an amino group in a manner known per se,

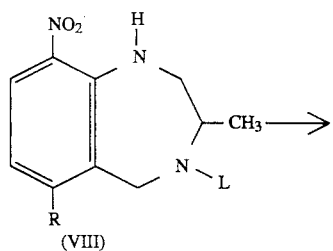
(VIII)

-continued

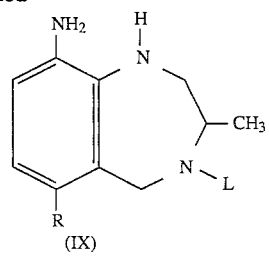
(IX)

(vi) condensing the 9-amino-6-halo-2,3,4,5-tetrahydro-1H-1,4-benzodiazepine of formula (IX) with carbon disulfide, 1,1'-carbonothionylbis[1H-imidazole], a xanthate and the like reagents, in a manner known per se, to a compound of formula (I), and optionally, if desired, convening the thus obtained compounds of formula (I) into therapeutically active non-toxic acid addition salt forms by treatment with an acid, or conversely, converting the acid addition salt form into the free base with alkali;

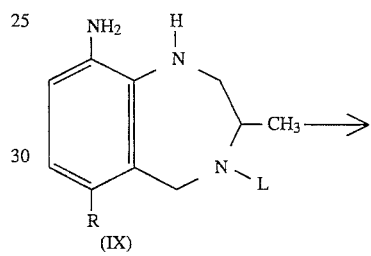
(IX)

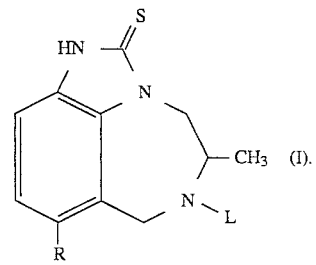
(I).

Reaction step (i) is preferably conducted by using enantiomerically pure 1,2-diaminopropane protected on $N^1$ by a sulfonyl group, in particular, 4-methylbenzenesulfonyl or 2,6-dimethylbenzenesulfonyl. The preferred (S)-enantiomers of the compounds of formula (I) are prepared from (S)-$N^1$-protected-1,2-diaminopropanes which are readily available from commercial (S)-1,2-diaminopropane by selective protection of the sterically least hindered primary amino group (reaction step o). For example, selective protection of $N^1$ can conveniently be effected by slow addition of a sulfonyl halide to an excess of 1,2-diaminopropane at a temperature ranging from about −10° C. to about 10° C., preferably from about 0° C. to about 5° C. The nitrated starting material of formula (II) wherein W represents halo can conveniently be prepared by nitrating a symmetrical 2,6-dihalobenzylhalide following art-known nitrating procedures. The corresponding starting materials of formula (II) wherein W represents a sulfonyloxy group are preferably prepared by nitrating a symmetrical 2,6-dihalobenzaldehyde, reducing the aldehyde to the alcohol and sulfonylating with a sulfonyl halide.

According to a preferred embodiment of the process of the present invention the deprotected amine of formula (V) is not isolated from the reaction mixture, but is cyclized immediately to the 9-nitro-6-halo-2,3,4,5-tetrahydro-1H-1,4-benzodiazepine of formula (VI) by diluting said reaction mixture with an alkanol such as, for example, ethanol, 2-propanol, 1-butanol and the like, alkalinizing with a base such as an alkali metal carbonate or hydroxide, e.g. sodium or potassium carbonate or hydroxide and the like bases, and stirring and heating the thus obtained basic reaction mixture, preferably at the reflux temperature. This one pot approach to reaction steps (ii) and (iii) excludes a number of manipulations and results in an increased yield.

In an interesting alternative, the intermediate of formula (IV) is not deprotected but directly cyclized to the benzodiazepine of formula (XIV) by a procedure similar to that described in reaction step (iii), i.e. by treating (IV) with a base, preferably at an elevated temperature.

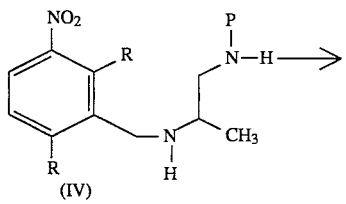

The intermediate of formula (XIV) may then be deprotected by hydrolysis as described in reaction step (ii) to yield an intermediate of formula (VI).

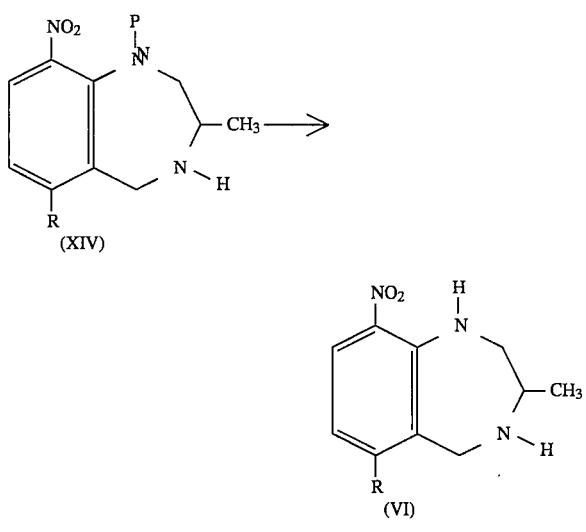

Thus steps (ii) and (iii) may well be conducted in reverse order. Alternatively, the protected benzodiazepine of formula (XIV) can also be N-alkylated with a reagent of formula (L—W) (VII) according to a procedure given in reaction step (iv), yielding an intermediate of formula (XV).

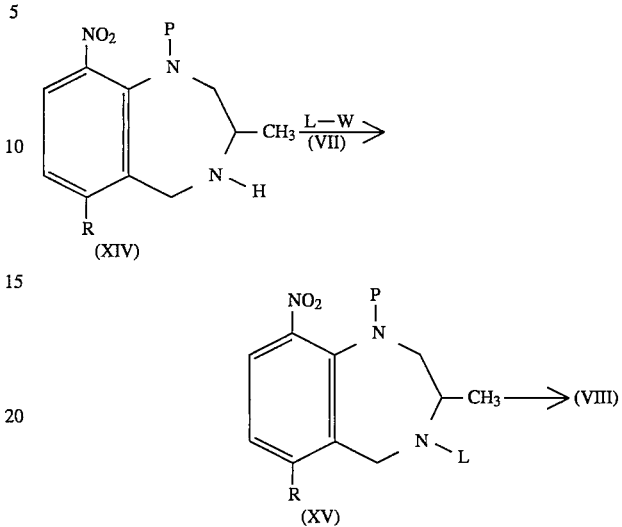

The intermediate of formula (XV) may then be deprotected by hydrolysis as described in reaction step (ii) to yield an intermediate of formula (VIII). Thus reaction step (ii) may also be conducted after first having conducted reaction steps (iii) and (iv).

The reaction steps (iv), (v) and (vi) of the present process are known per se from, for example, EP-A-0,348,522 and WO-91/04255. The N-alkylation procedure (iv) can conveniently be conducted in solvent such as an aromatic hydrocarbon, e.g. methylbenzene, an alcohol, e.g. 1-butanol, a ketone, e.g. acetone or preferably 4-methyl-2-pentanone, a dipolar aprotic solvent, e.g. N,N-dimethylformamide, N,N-dimethylacetamide, dimethyl sulfoxide and the like, or a mixture of such solvents. Appropriate bases for use in said process are alkali metal carbonates or hydrogen carbonates, or preferably organic bases such as, for example, N,N-diethylethanamine, N-(1-methyl-ethyl)-2-propanamine and the like. The reduction procedure (v) can conveniently be conducted by treating the nitro compound (VI) with platinum or Raney nickel catalyst in an alcohol, preferably methanol, under a hydrogen atmosphere at room temperature and at normal pressure, or alternatively with Raney nickel catalyst and hydrazine at an elevated temperature, in particular at the reflux temperature of the reaction mixture. The ultimate cyclization step (vi) is preferably conducted by treating intermediate (IX) with a thiocarbonyl generating reagent as described in EP-A-0,348,522. For example, said cyclization can be conducted with carbon disulfide in an alcohol such as methanol, ethanol and the like, in the presence of a base such as sodium or potassium hydroxide and the like, at an elevated temperature, in particular at about 50° to 80° C. Alternatively, said cyclization can also be conducted by treating (IX) with 1,1'-carbonothionylbis-[1H-imidazole] in an alcohol such as ethanol, 2-propanol and the like or in an ether such as tetrahydrofuran, 1,1'-oxybisethane and the like, optionally at an elevated temperature and under an inert atmosphere.

A viable alternative for converting the intermediates of formula (VI) into the compounds of formula (I) comprises the following reaction steps:

(vii) reducing the nitroderivate of formula (VI) to an amino derivate (X) in a manner known per se,

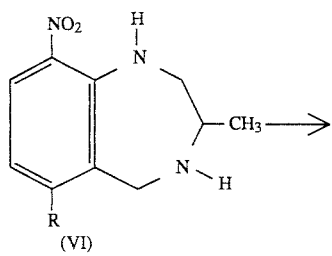

(VI)

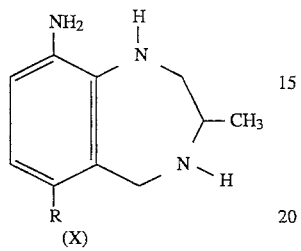

(X)

(viii) cyclizing the thus obtained 9-amino-6-halo-2,3,4,5-tetrahydro-1H-1,4-benzodiazepine (X) to the corresponding 8-halo-4,5,6,7-tetrahydro-5-methyl-imidazo[4,5,1-jk][1,4]benzodiazepin-2-one (XI) with a carbonyl generating reagent such as, for example, ethyl chloroformate and the like in a manner known per se, and optionally convening (XI) into an acid addition salt form,

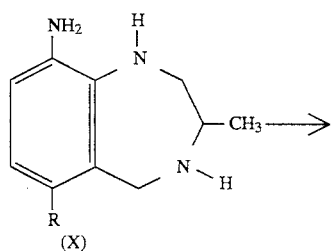

(X)

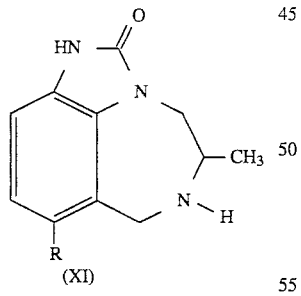

(XI)

(ix) convening the intermediate (XI) or an acid addition salt form thereof, into the corresponding 2,8-dihaloimidazo[4,5,1-jk][1,4]benzodiazepine (XII) by treatment with an excess of a halogenating reagent such as, for example, phosphorylchloride, and the like, at an elevated temperature, in particular from about 75° C. to about 105° C.,

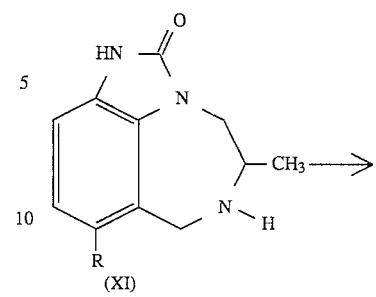

(XI)

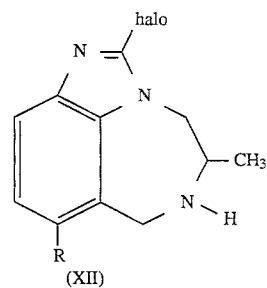

(XII)

(x) N-alkylating the intermediate (XII) with an alkylating reagent of formula L—W (VII) as defined hereinabove in a reaction-inert solvent in the presence of a base and optionally in the presence of an alkali metal iodide; and optionally further converting (XIII) into an acid addition salt form,

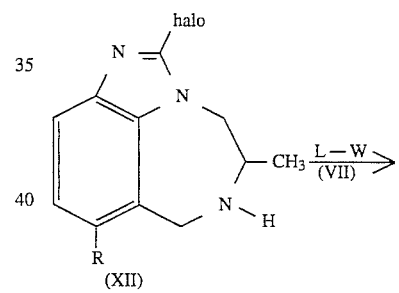

(XII)

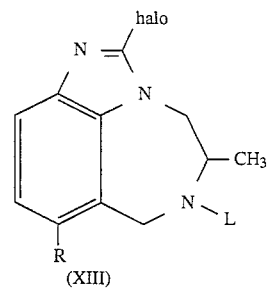

(XIII)

(xi) convening the dihalo intermediate (XIII) or preferably an acid addition salt form thereof, into a compound of formula (I) in a manner known per se, i.e. by heating (XIII) with thiourea in an alcohol such as, for example, ethanol, 2-propanol and the like, and optionally, convening the thus obtained compounds of formula (I) into therapeutically active non-toxic acid addition salt forms by treatment with an acid, or conversely, convening the acid addition salt form into the free base with alkali;

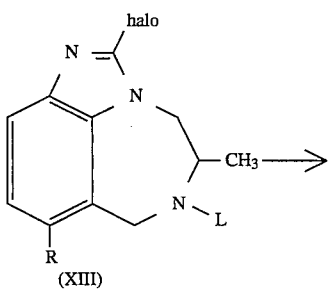

(XIII)

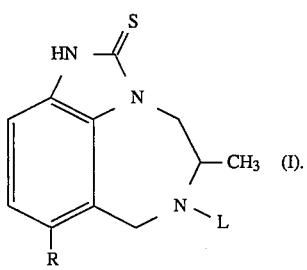

The alternative approach represented by reaction steps (vii–xi) is especially attractive by the fact that the integrity of the $C_{3-7}$alkenyl group L, in particular the position of the double bond, can be maintained effortlessly. The reaction steps (vii), (viii), (ix) and (xi) are known per se from, for example, EP-A-0,348,522 and WO-91/04255. The N-alkylation procedure (x) on intermediate (XII) is novel and can conveniently be conducted following art-known procedures, such as the procedures described in reaction step (iv) hereinabove. A surprising effect in the ultimate step (xi) relates to the use of acid addition salt forms of (XIII): whereas the base form reacts only sluggishly with thiourea, the acid addition forms react quite rapidly. This simple modification results in a considerably shortened reaction time.

The key intermediates of formula (III) and (IV) used in the process according to the present invention are deemed novel. Consequently, the present invention also concerns enantiomerically pure intermediates having the formulae

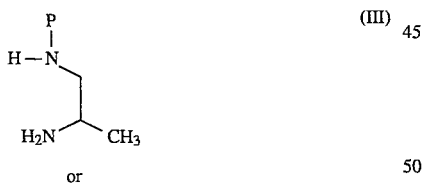

or

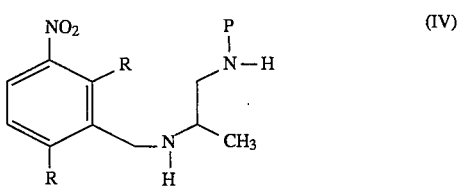

and acid addition salt forms thereof, wherein

R represents halo, and

P represents a sulfonyl group or an acyl group.

Preferred key intermediates are those wherein

R represents chloro or bromo, and

P represents benzenesulfonyl, 4-methylbenzenesulfonyl or 2,6-dimethylbenzenesulfonyl.

The following examples serve to further illustrate the present invention without however limiting the same thereto. Unless otherwise stated, all parts therein are by weight.

EXPERIMENTAL PART

Example 1

To 62.9 parts of (S)-1,2-propanediamine under a nitrogen atmosphere (temp. 0°–5° C.) was added dropwise over 7 hours a solution of 80.84 parts of 4-methylbenzenesulfonyl chloride in 1689 parts of dichloromethane. After stirring overnight at 20° C., the reaction mixture was washed with 250 parts of water (3x). The organic layer was separated, dried, filtered and evaporated. About 1 gram of the thus obtained product was recrystallized from 2-propanol. After cooling to 0° C., filtering and drying, about 0.30 parts of crystals suitable for seeding were obtained. The remainder of the product was dissolved in 4-methyl-2-pentanol by heating just below the reflux temperature. The mixture was allowed to cool slowly and at about 30° C. was seeded with the previously obtained crystals. After further cooling to 0° C., the precipitate was filtered off and triturated with 2,2'-oxybispropane. The crystals were filtered off, dried in vacuo, yielding 50.75 parts (52.4%) of (S)-N-2-aminopropyl-4-methylbenzenesulfonamide; mp. 82°–86° C.; $[\alpha]_D^{20}=-1.10°$ (c=1% in methanol) (interm. 1)

Example 2

At 12° C., sulfuric acid (89 ml) was added to nitric acid (114 ml), giving solution 1. 2-chloromethyl-1,3-dichlorobenzene (1.45 mol) was melted in a vacuum oven at 50° C. (mp:36°–39° C.). 2-chloromethyl-1,3-dichlorobenzene (1.45 mol) was added to sulfuric acid (829.2 ml) at 15° C., giving mixture 2 (precipitation occurred). Solution 1 was added dropwise to mixture 2 over a 35 min. period, at 22°–25° C. (exothermic reaction, emulsification). The reaction mixture was stirred for 90 min. at 23° C. The reaction mixture was poured out into ice/water (2250 g/500 ml) (exothermic temperature rise to 22° C.). The mixture was stirred for 90 min. at 23° C. The precipitate was filtered off, washed with water and dried (vacuum;30° C.), yielding 342.1 g (98.1%)of 1,3-dichloro-2-(chloromethyl)-4-nitrobenzene (interm. 2).

Example 3 a) To a solution of 6.0 parts of intermediate (2) in 44.5 parts of tetrahydrofuran were added 5.82 parts of intermediate (1) and 3.04 parts of N,N-diethylethanamine. The whole was stirred for 45 hours at reflux temperature. After cooling to room temperature, the reaction mixture was filtered. The filtrate was dried, filtered and evaporated. The residue was taken up in dichloromethane and washed with water (3x). The organic layer was dried, filtered and evaporated, yielding 10.81 parts (100%) of (S)-N-[2-[[(2,6-dichloro-3-nitrophenyl) methyl]amino]propyl]-4-methylbenzenesulfonamide; mp. 85°–88° C.; $[\alpha]_D^{20}=+9.15°$ (c=1% in methanol) interm.3).

b) To a solution (20° C.) of 2 parts of (2,6-dichloro-3-nitrophenyl)methanol methanesulfonate in 26.6 parts of dichloromethane were added dropwise 0.68 parts of N,N-diethylethanamine and a solution of 1.52 parts of intermediate (1) in 13.3 parts of dichloromethane. After stirring for 24 hours at reflux temperature, the reaction mixture was washed with water (3x). The organic layer was separated, dried, filtered and evaporated. The product was dried in vacuo at 50° C., yielding 2.77 parts (96.1%) of (S)-N-[2-[[(2,6 -dichloro-3-nitrophenyl)methyl]amino]propyl]-4-methylbenzenesulfonamide (interm. 3).

Example 4

To a mixture of 5 parts of intermediate (3) and 11.7 parts of sulfuric acid were added dropwise 1.15 parts of water. After stirring for 24 hours at 100° C. and cooling, there were added 33.25 parts of dichloromethane. The reaction mixture was cooled to 0° C. and there was added water (temp. 0°–5° C.). The reaction mixture was basified with NaOH. The aqueous layer was separated and extracted with dichloromethane. The combined organic layers were dried, filtered and evaporated. The residue was convened into the dihydrochloride salt in 2-propanol saturated with hydrochloric acid. The product was filtered off and dried, yielding 3.34 parts (82.3%) of (S)-$N^2$-[(2,6-dichloro-3-nitrophenyl)methyl-1,2-propanediamine dihydrochloride (interm. 4).

Example 5 a) To a solution of 2 parts of intermediate (4) in 11.7 parts of 2-propanol were added dropwise 2.88 parts of N,N-diethylethanamine. After refluxing for 10 hours, the reaction mixture was evaporated and dried in vacuo at 50° C. The residue was partitioned between dichloromethane and water. Then there were added a few drops of N,N-diethylethanamine until pH>9. The organic layer was separated, washed with water, dried, filtered and evaporated, yielding 1.32 parts (95.9%) of (S)-6-chloro-2,3,4,5-tetrahydro-3-methyl-9-nitro-1H-1,4-benzodiazepine (interm.5).

b) A solution of 49 parts of intermediate (3) in 116.8 parts of sulfuric acid was warmed up to 80° C. Then there were added dropwise 11.3 parts of water and the whole was stirred for 30 hours at 100° C. After cooling there were added 222.3 parts of 2-propanol and portionwise 144.1 parts of sodium carbonate. The whole was stirred for 5 hours at reflux temperature. The reaction mixture was evaporated and the residue was partitioned between dichloromethane and water. The whole was filtered and the organic layer was separated and washed with water (2×). The combined organic layers were dried, filtered and evaporated at 50° C., yielding 23.74 parts (86.7%) of (S)-6-chloro-2,3,4,5-tetrahydro-3-methyl-9-nitro- 1H-1,4-benzodiazepine (interm. 5).

Example 6

A mixture of 1 part of intermediate (5) and 59.25 parts of methanol was hydrogenated at normal pressure and at 20° C. in the presence of 0.082 parts of platinum-on-charcoal catalyst 5%. After the calculated amount of hydrogen was taken up, the catalyst was filtered off over diatomaceous earth and the filtrate was evaporated. The product was dried in vacuo at 45° C., yielding 0.87 parts (99.3%) of (S)-6-chloro-2,3,4,5-tetrahydro-3-methyl -1H-1,4-benzodiazepin-9-amine (interm. 6).

Example 7

To a cooled mixture (ice-bath) of 0.77 parts of sodium carbonate and 0.70 parts of intermediate (6) in 0.66 ml of propylene glycol monomethyl ether were added dropwise 0.79 parts of ethyl chloroformate. The whole was stirred for 2 hours at 20° C. and then refluxed for 20 hours. The reaction mixture was cooled to 80° C. and 2.64 parts of NaOH 50% were added. Refluxing was continued for 24 hours. After cooling (50° C.), water was added and the whole was stirred for 1 hour. The aqueous layer was separated and extracted with polyglycol monomethyl ether and the combined organic layers were neutralized with HCl, yielding 0,785 parts (99.9%) of (S)-8-chloro-4,5,6,7-tetrahydro-5-methylimidazo[4,5,1-jk][1,4]benzodiazepin-2(1H)-one (interm. 7).

Example 8

13 parts of intermediate (7) was converted into the hydrochloride salt in 2-propanol saturated with hydrochloric acid. The precipitate was filtered off and washed with 2-propanol, yielding 13.5 parts (90.0%) of product. The mother liquor was evaporated and dried at 50° C., yielding another 0.58 parts (3.8%) of product. Total yield: 14.08 parts (93.9%) of (S)-8-chloro-4,5,6,7-tetrahydro-5-methylimidazo[4,5,1-jk][1,4]-benzodiazepin-2(1H)-one monohydrochloride (interm. 8).

Example 9

At 20° C., 2 parts of intermediate (8) were suspended in 29.7 parts of phosphoryl chloride. The suspension was warmed up to 90° C. and there were added another 42.6 parts of phosphoryl chloride. The reaction mixture was filtered at 20° C. and the filtrate was evaporated. The residue was taken up in 180 parts of ethyl acetate. At 0°–5° C. the mixture was basified with a solution of sodium hydrogen carbonate in water and stirring was continued for 1 hour at this temperature. The whole was filtered and washed with ethyl acetate. The aqueous layer was separated and re-extracted with ethyl acetate. The combined organic layers were washed with water, dried, filtered and evaporated, yielding 1.07 parts (57.3%) of (S)-2,8-dichloro-4,5,6,7-tetrahydro-5-methylimidazo[4,5,1-jk][1,4]benzodiazepine (interm. 9).

Example 10

To a stirred mixture of 5.5 parts of intermediate (9), 89.1 parts of dichloromethane, 3.42 parts of sodium carbonate, 18.8 parts of N,N-dimethylformamide and 3.57 parts of potassium iodide were added dropwise 2.39 parts of N,N-diethylethanamine and 41.94 parts 1-chloro-3-methyl-2-butene in 65.25 parts of methylbenzene. After refluxing for 48 hours, the reaction mixture was washed with water (5×). The organic layer was separated, dried, filtered and evaporated. The residue wag converted into the hydrochloride salt in 2-propanol saturated with hydrochloric acid. The salt was filtered off at 0°–5° C. and dried in vacuo at 29° C., yielding 5.18 parts (66.8%) of product. The mother liquor was stirred for 24 hours at 20° C., filtered off, washed and dried, yielding another 0.49 parts (6.3%)of product. Total yield:5.67 parts (73.1%)of (S)-2,8- dichloro-4,5,6,7-tetrahydro-5-methyl-6-(3-methyl-2-butenyl)imidazo[4,5,1-jk][ 1,4] -benzodiazepine dihydrochloride (interm. 10).

Example 11 a) To a solution (20° C.) of 2.5 parts of intermediate (10) in 12.6 parts of ethanol were added 0.53 parts of thiourea. After stirring for 1.5 hours at reflux temperature, the reaction mixture was cooled to 0°–5° C. and filtered off at 0° C. The residue was dried in vacuo at 30° C., yielding 1.70 parts (75.4%) of (−)-(S)-8-chloro-4,5,6,7-tetrahydro-5-methyl-6(3-methyl-2-butenyl)imidazo[4,5,1-jk][1,4]benzodiazepin-2(1H)-thione monohydrochloride; mp. 230° C.; $[\alpha]_D^{20}$=−76.61° (c=1% in methanol) (comp. 1).

b) 0.5 Parts of compound (1) were partitioned between dichloromethane and water. The whole was basified with NH₄OH. The organic layer was separated, dried, filtered and evaporated. The product was dried in vacuo at 40° C., yielding 0.43 parts (95.7%) of (+)-(S)-8-chloro-4,5,6,7-tetrahydro-5-methyl-6-(3-methyl-2-butenyl)imidazo[4,5,1-jk]-[1,4]benzodiazepin-2(1H)-thione; mp. 160° C.; $[\alpha]_D^{20}$=+9.97° (c=1% in methanol (comp. 2).

Example 12

To a mixture of 11.30 parts of intermediate (5), 56 parts of 4-methyl-2-pentanone, 3.88 parts of potassium iodide and 14.85 parts of sodium carbonate were added dropwise 119.7 parts of 1-chloro-3-methyl-2-butene. After refluxing for 3 hours, the reaction mixture was diluted with water. The whole was stirred for 30 minutes. The aqueous layer was separated and re-extracted with 4-methyl-2-pentanone. The combined organic layers were dried, filtered and evaporated. The residue was purified by column chromatography (silicagel: eluens CH₂Cl₂), yielding 7.72 parts (53.3%) (S)-6-chloro-2,3,4,5 -tetrahydro-3-methyl-4-(3-methyl-2-butenyl)-9-nitro- 1H-1,4-benzodiazepine; mp. 60°–62° C.; $[\alpha]_D^{20}$=+118.53° (c=1% in methanol) (interm. 11).

In a similar way there were prepared:
[S,(Z)]-4-(2-butenyl)-6-chloro-2,3,4,5-tetrahydro-3-methyl-9-nitro-1H-1,4-benzodiacepin e(interm. 13);
(S)-6-chloro-2,3,4,5-tetrahydro-3-methyl-4-(2-methyl-2-propenyl)-9-nitro-1H-1,4-benzodiazepine (interm. 14);
[S,(E)]-4-(2-butenyl)-6-chloro-2,3,4,5-tetrahydro-3-methyl-9-nitro-1H-1,4-benzodiazepine (interm. 15);
[S,(E)]-6-chloro-4-(2-ethyl-2-butenyl)-2,3,4,5-tetrahydro-3-methyl-9-nitro-1H-1,4-benzodiazepine (interm. 16);
[S,(Z)]-6-chloro-2,3,4,5-tetrahydro-3-methyl-9-nitro-4-(2-pentenyl)-1H-1,4-benzodiazepine (interm. 17);
[S,(Z)]-6-chloro-4-(3-hexenyl)-2,3,4,5-tetrahydro-3-methyl-9-nitro-1H-1,4-benzodiazepine (interm. 18);
[S,(E)]-6-chloro-4-(2-hexenyl)-2,3,4,5-tetrahydro-3-methyl-9-nitro- 1H-1,4-benzodiazepine (interm. 19);
[S,(E)]-6-chloro-4-(3-hexenyl)-2,3,4,5-tetrahydro-3-methyl-9-nitro-1H-1,4-benzodiazepine (interm. 20);
(S)-4-(3-butenyl)-6-chloro-2,3,4,5-tetrahydro-3-methyl-9-nitro-1H-1,4-benzodiazepine (interm. 21 ); and
(S)-6-fluoro-2,3,4,5-tetrahydro-3-methyl-4-(3-methyl-2-butenyl)-9-nitro-1H-1,4-benzodiazepine (interm. 22).

Example 13 a) A solution of 2.16 parts of intermediate (11) in 67.2 parts of ethanol was hydrogenated overnight at normal pressure and room temperature in the presence of a few parts of Raney nickel. The catalyst was filtered off and washed with ethanol. The combined filtrates were evaporated and the residue was washed with water, dried, filtered and evaporated, yielding 1.9.6 parts (100%) of (S)-6-chloro-2, 3,4,5-tetrahydro-3-methyl-4-(3-methyl-2-butenyl)-1H-1,4-benzodiazepin-9-amine (interm. 12) b) To a solution of 0.5 parts of intermediate (11) in methanol there were added 0.2 parts of Raney nickel. To the resulting suspension there was added a solution of 0.35 parts of hydrazine in a small amount of methanol and the reaction mixture was refluxed for 1.5 hours under an inert atmosphere. After cooling, the catalyst was filtered off and the filtrate was evaporated, yielding (S)-6-chloro-2,3,4,5-tetrahydro-3-methyl-4-(3-methy-2-butenyl)-1H-1,4-benzodiaepin-9-amine (interm. 12). In a similar way there were prepared:
(S)-6-chloro-2,3,4,5-tetrahydro-3-methyl-4-(2-methyl-2-propenyl)-1H-1,4-benzodiazepin-9-amine (interm. 23);
[S,(E)]-4-(2-butenyl)-6-chloro-2,3,4,5-tetrahydro-3-methyl-1H-1,4-benzodiazepin-9-amine (interm. 24);
(S)-6-fluoro-2,3,4,5-tetrahydro-3-methyl-4-(3-methyl-2-butenyl)-1H-1,4-benzodiazepin-9-amine (interm. 25);
[S,(E)]-6-chloro-4-(2-ethyl-2-butenyl)-2,3,4,5-tetrahydro-3-methyl-1H-1,4-benzodiazepin-9-amine (interm. 26);
[S,(Z)]-6-chloro-2,3,4,5-tetrahydro-3-methyl-4-(2-pentenyl)-1H-1,4-benzodiazepin-9-amine (interm. 27);
[S,(Z)]-6-chloro-4-(3-hexenyl)-2,3,4,5-tetrahydro-3-methyl-1H-1,4-benzodiazepin-9-amine (interm. 28); and
[S,(Z)]-4-(2-butenyl)-6-chloro-2,3,4,5-tetrahydro-3-methyl-1H-1,4-benzodiazepin-9-amine (interm. 29).

c) Lithium aluminum hydride (30 ml) was stirred under argon flow. Intermediate (20) (0.005 mol) was dissolved in tetrahydrofuran (15 ml) and this solution was added dropwise to the reaction mixture (colour change; slight exothermic reaction). The reaction mixture was allowed to warm up to room temperature and was stirred for 6 hours. 3N NaOH (2.55 ml) was added cautiously and dropwise (foaming, colour change; exothermic reaction). The reaction mixture was stirred for 0.5 hours and filtered over dicalite. The filtrate was evaporated. The residue (1.58 g; oil) was purified by flash column chromatography over silica gel (eluent: CH₂Cl₂/CH₃OH 100/0 upgrading to 98/2). The pure fractions were collected and evaporated, yielding 0.93 g (63%) of
[S,(E)]-6-chloro-4-(3-hexenyl)-2,3,4,5-tetrahydro-3-methyl-1H-1,4-benzodiazepin-9-amine (interm. 30);
In a similar way there were prepared:
[S,(E)]-6-chloro-4-(2-hexenyl)-2,3,4,5-tetrahydro-3-methyl-1H-1,4-benzodiazepin-9-amine (interm. 31 ); and
(S)-4-(3-butenyl)-6-chloro-2,3,4,5-tetrahydro-3-methyl-1H-1,4-benzodiazepin-9-amine (interm. 32)

Example 14 a) A mixture of 0.295 parts of intermediate (12), 0.0056 parts of potassium hydroxide, 0.79 parts of ethanol and 0.06 parts of carbon disulfide was stirred for 18 hours at 60° C. After cooling, there was added trichloromethane and the whole was filtered. The filtrate was evaporated and the residue was purified by colomn chromatography (silicagel; eluens: CHCl₃/CH₃OH; 99.5:0.5). The eluent of the desired fraction was filtered and evaporated and the residue was triturated in 3.95 parts of acetonitrile under a nitrogen atmosphere. The product was filtered off and dried under a nitrogen atmosphere, yielding 0.308 parts (91.1%) of (+)-(S)-8-chloro-4,5,6,7-tetrahydro-5-methyl-6-(3-methyl-2-butenyl)imidazo-[4,5,1-jk][1,4]benzodiazepin-2(1H)-thione (comp. 2). b) To a solution of 1.69 parts of intermediate (12) in 14.0 parts of 2-propanol there were added 1.18 parts of 1,1'-carbonothionylbis[1H-imidazole]. The whole was homogenized and then left for ½ hour to crystallize. The product was filtered off, washed with 2-propanol and dried in vacuo, yielding 0.92 parts (47.6%). The mother liquor was stirred overnight at 0°–5° C. A second product fraction was filtered off, washed and dried, yielding 0.26 parts (13.5%). Total yield: 1.18 parts (61.1%) of (+)-(S)-8-chloro-4,5,6,7-tetrahydro-5-methyl-6-(3-methyl-2butenyl)imidazo-[4,5,1-jk] [1,4]benzodiazepin-2(1H)-thione; $[\alpha]\alpha_D^{20}$ =+8.98° (conc.=1% in methanol) (comp 2). c) To a flask under argon was added 1.75 g of intermediate (12) in 35 ml of tetrahydrofuran and 1.40 g of 1,1'-carbonothionylbis[1H-imidazole]. The reaction mixture was refluxed for 0.5 hours, the solvent evaporated and the residue flash chromatographed with 0.5% CH₃Oh/CH₂Cl₂ to give 2 g of product. One recrystallization with ethanol gave 1.03 g (54%) of (+)-(S)-

8-chloro-4,5,6,7-tetrahydro-5-methyl-6-(3-methyl-2-butenyl)imidazo-[4,5,1-jk][1,4]benzodiazepin-2(1H)-thione; mp. 163.3° C. (comp. 2).

In a similar way were prepared:

(+)-[S,(Z)]-8-chloro-6-(3-hexenyl)-4,5,6,7-tetrahydro-5-methylimidazo-[4,5,1-jk] [1,4]benzodiazepin-2(1H)-thione; mp. 139.40° C.;

$[\alpha]_D^{20}=+9.84°$ (conc.=0.64% in trichloromethane) (comp. 3);

(+)-[S,(E)]-8-chloro-6-(2-hexenyl)-4,5,6,7-tetrahydro-5-methylimidazo-[4,5,1-jk] [1,4]benzodiazepin-2(1H)-thione; 142.9° C.;

$[\alpha]_D^{20}=+3.54°$ (conc.=0.48% in methanol) (comp. 4);

(+)-[S,(E)]-8-chloro-6-(3-hexenyl)-4,5,6,7-tetrahydro-5-methylimidazo-[4,5,1-jk] [1,4]benzodiazepin-2(1H)-thione; mp. 144.4° C.;

$[\alpha]_D^{20}=+12.46°$ (conc.=0.69% in methanol) (comp. 5);

(+)-(S)-6-(3-butenyl)-8-chloro-4,5,6,7-tetrahydro-5-methylimidazo-[4,5,1-jk] [1,4]benzodiazepin-2(1H)-thione; mp. 170.4° C.;

$[\alpha]_D^{20}=+6.11°$ (conc.=0.36% in methanol) (comp. 6);

(+)-[S,(Z)]-6-(2-butenyl)-8-chloro-4,5,6,7-tetrahydro-5-methylimidazo-[4,5,1-jk] [1,4]benzodiazepin-2(1H)-thione; mp. 159.6° C.;

$[\alpha]_D^{20}=+12.67°$ (conc.=0.1% in methanol) (comp. 7);

(+)-(S)-8-fluoro-4,5,6,7-tetrahydro-5-methyl-6-(3-methyl-2-butenyl)imidazo-[4,5,1-jk] [1,4]benzodiazepin-2(1H)-thione; mp. 172.1 ° C.;

$[\alpha]_D^{20}=+5°$ (conc.=1% in methanol) (comp. 8);

(+)-[S,(E)]-6-(2-butenyl)-8-chloro-4,5,6,7-tetrahydro-5-methylimidazo-[4,5,1-jk] [1,4]benzodiazepin-2(1H)-thione; 159.2° C.;

$[\alpha]_D^{20}=+1.2°$ (conc.=0.83% in methanol) (comp. 9);

(+)-[S,(E)]-8-chloro-6-(2-ethyl-2-butenyl)-4,5,6,7-tetrahydro-5-methylimidazo-[4,5,1-jk ][1,4]benzodiazepin-2(1H)-thione; mp. 163.6° C.;

$[\alpha]_D^{20}=+17.7°$ (conc. =0.1% in methanol) (comp. 10);

(+)-[S,(Z)]-8-chloro-4,5,6,7-tetrahydro-5-methyl-6-(2-pentenyl)imidazo-[4,5,1-jk] [1,4]benzodiazepin-2(1H)-thione; mp. 143.1 ° C.;

$[\alpha]_D^{20}=+9.19°$ (conc.=0.1% in methanol) (comp. 11); and (−)-(S)-8-chloro-4,5,6,7-tetrahydro-5-methyl-6-(2-methyl-2-propenyl)imidazo-[4,5,1-jk] [1,4]benzodiazepin-2(1H)-thione monohydrochloride; mp. 207.6° C.;

$[\alpha]_D^{20}=-33.01°$ (conc.=0.1% in methanol) (comp. 12).

We claim:

1. A process for preparing an enantiomerically pure 8-halo-4,5,6,7-tetrahydro-5-methylimidazo[4,5,1-jk] [ 1,4] benzodiazepin-2-(1H)-thione of the formula:

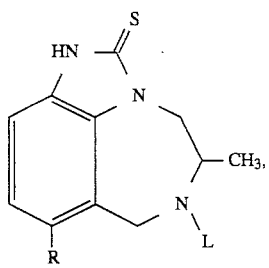

(I)

or a pharmaceutically acceptable acid addition salt form thereof, wherein:

R represents halo; and L represents $C_{3-7}$ alkenyl, wherein said process comprises the steps of:

(a) selectively protecting enantiomerically pure 1,2-diaminopropane by reaction with a protecting group of the formula P—W wherein P represents a protecting group selected from the group consisting of sulfonyl and acyl, and W represents a reactive leaving group selected from the group consisting of halo and sulfonyloxy, to produce an intermediate of Formula (III):

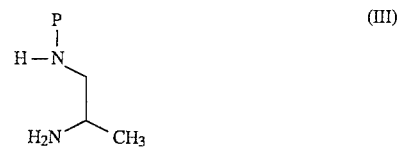

wherein P is as defined above:

(b) reacting a 2,6-dihalo-3-nitrobenzyl derivative of the formula:

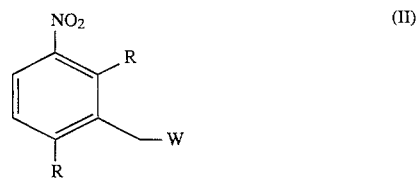

wherein R represents halo and W represents a reactive leaving group selected from the group consisting of halo and sulfonyloxy, with an enantiomerically pure $N^1$-protected 1,2-diaminopropane derivative of Formula (III) in an inert reaction vehicle in the presence of a base, to produce an intermediate of the formula:

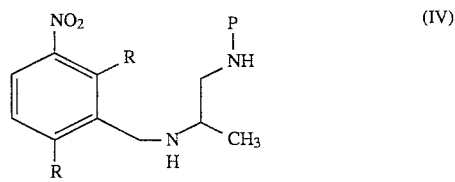

wherein P and R are as defined above;

(c) deprotecting the thus obtained intermediate of Formula (IV) in an acidic medium, to produce an intermediate of the formula:

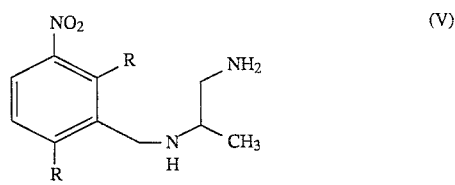

or its acid addition salt, wherein R is as defined above;

(d) cyclizing the intermediate of Formula (V) or its acid addition salt by treatment with a base in an inert reaction vehicle at an elevated temperature sufficient to effect the cyclization, to thereby produce a benzodiazepine of the formula:

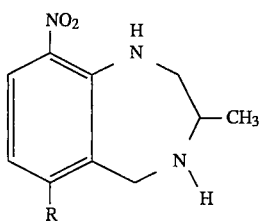

wherein R is as defined above;

(e) N-alkylating the benzodiazepine of Formula (VI) with an alkylating reagent of formula L—W wherein L is $C_{3-7}$alkenyl and W is a reactive leaving group selected from the group consisting of halo and sulfonyloxy, in an inert reaction vehicle in the presence of a base at an elevated temperature sufficient to effect the N-alkylation, to produce thereby an intermediate of Formula (VIII):

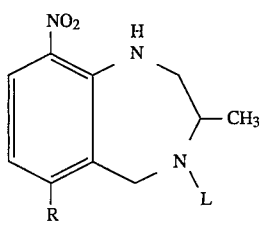

wherein L and R are as defined above;

(f) selectively reducing the nitro group in the compound of Formula (VIII) by treatment with a reducing agent, to produce an intermediate of Formula (IX):

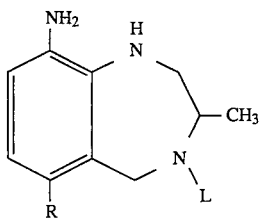

wherein L and R are as defined above; and (g) condensing the intermediate of Formula (IX) with carbon disulfide, 1,1'-carbonothionylbis or a xanthate, to produce a compound of Formula (I).

2. A process according to claim 1 wherein the compound of formula (I) has the formula

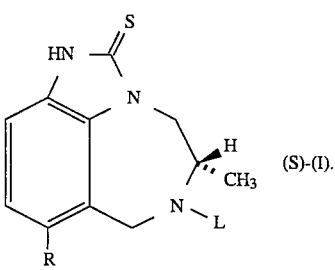

3. A process according to claim 2 wherein R represents chloro or bromo; and L represents 3-methyl-2-butenyl or 3-ethyl-2-pentenyl.

4. A process according to claim 3 wherein the compound of formula (I) is (S)-8-chloro-4,5,6,7-tetrahydro-5-methyl-6-(3-methyl-2-butenyl)imidazo[4,5,1-jk]-[1,4]benzodiazepine-2(1H)-thione or an acid addition salt thereof.

5. A process according to claim 1 wherein a one pot approach to reaction steps (c) and (d) is employed.

6. A process according to claim 1 wherein reaction steps (c) and (d) are conducted in reverse order.

7. The process of claim 1 wherein the N-alkylation of step (e) is carried out in the presence of an alkali metal iodide.

8. A process for preparing an enantiomerically pure 8-halo-4,5,6,7-tetrahydro-5-methylimidazo [4,5,1-jk][1,4] benzodiazepin-2--(1H)-thione of the formula:

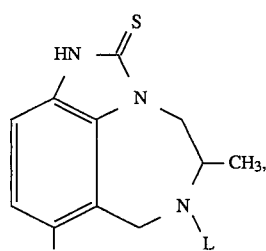

or a pharmaceutically acceptable acid addition salt form thereof, wherein:

R represents halo; and

L represents $C_{3-7}$alkenyl, wherein said process comprises the steps of:

(a) selectively protecting enantiomerically pure 1,2-diaminopropane by reaction with a protecting group of the formula P—W wherein P represents a protecting group selected from the group consisting of sulfonyl and acyl, and W represents a reactive leaving group selected from the group consisting of halo and sulfonyloxy, to produce an intermediate of Formula (III):

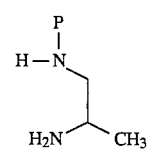

wherein P is as defined above:

(b) reacting a 2,6-dihalo-3-nitrobenzyl derivative of the formula:

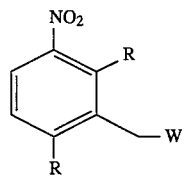

wherein R represents halo and W represents a reactive leaving group selected from the group consisting of halo and sulfonyloxy, with an enantiomerically pure $N^1$-protected 1,2-diaminopropane derivative of Formula (III) in an inert reaction vehicle in the presence of a base, to produce an intermediate of the formula:

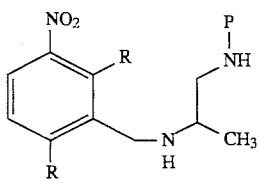

(IV)

wherein P and R are as defined above;

(c) deprotecting the thus obtained intermediate of Formula (IV) in an acidic medium, to produce an intermediate of the formula:

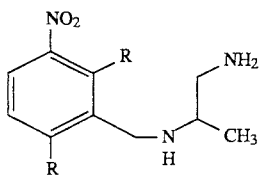

(V)

or its acid addition salt, wherein R is as defined above;

(d) cyclizing the intermediate of Formula (V) or its acid addition salt by treatment with a base in an inert reaction vehicle at an elevated temperature sufficient to effect the cyclization, to thereby produce a benzodiazepine of the formula:

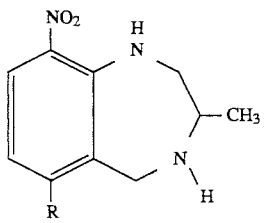

(VI)

wherein R is as defined above;

(e) reducing the benzodiazepine of Formula (VI) by treatment with a reducing agent to produce an amino derivative of the formula:

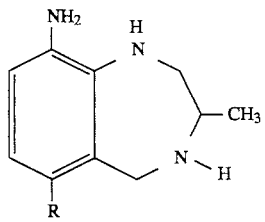

(X)

wherein R is as defined above;

(f) cyclizing the amino derivative of Formula (X) with a carbonyl generating reagent to produce a compound of the formula:

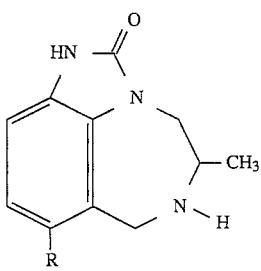

(XI)

wherein R is as defined above;

(g) treating the compound of Formula (XI) or an acid addition salt thereof with a halogenating reagent at an elevated temperature sufficient to halogenate said compound of Formula (XI) to produce a compound of the formula:

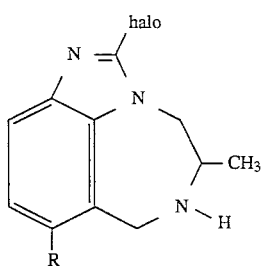

(XII)

wherein R is as defined above and "halo" represents a halo group; (h) N-alkylating the compound of Formula (XII) with an alkylating reagent of formula L—W wherein L is $C_{3-7}$alkenyl and W is a reactive leaving group in an inert reaction vehicle in the presence of a base at an elevated temperature sufficient to effect the N-alkylation, for produce thereby a compound of the formula:

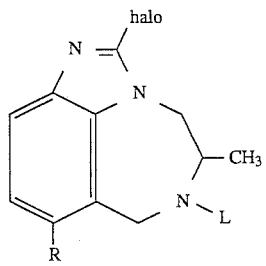

(XIII)

wherein R, L and halo are as defined above; and (i) reacting the compound of Formula (XIII) or an acid addition salt thereof with thiourea in an alcohol at an elevated temperature sufficient to produce a compound of Formula (I).

9. A process according to claim 8 wherein the compound of formula (I) is (S)-8-chloro-4,5,6,7-tetrahydro-5-methyl-6-(3-methyl-2-butenyl)imidazo[4,5,1-jk]-[1,4]benzodiazepine-2(1H)-thione or an acid addition salt thereof.

10. The process of claim 8 wherein the N-alkylation of step (h) is carried out in the presence of an alkali metal iodide.

* * * * *